(12) United States Patent
Reinbergen

(10) Patent No.: US 6,471,741 B1
(45) Date of Patent: Oct. 29, 2002

(54) LIQUID SOIL ENRICHMENT MICROBIAL COMPOSITIONS

(75) Inventor: Clare H. Reinbergen, Growth Products Ltd., 179 Westmoreland Ave., White Plains, NY (US) 10606

(73) Assignee: Clare H. Reinbergen, White Plains, NY (US)

( * ) Notice: Subject to any disclaimer, the term of this patent is extended or adjusted under 35 U.S.C. 154(b) by 0 days.

(21) Appl. No.: 09/117,718
(22) PCT Filed: Feb. 28, 1997
(86) PCT No.: PCT/US97/03128
§ 371 (c)(1),
(2), (4) Date: Aug. 5, 1998
(87) PCT Pub. No.: WO97/31879
PCT Pub. Date: Sep. 4, 1997

Related U.S. Application Data
(60) Provisional application No. 60/012,464, filed on Feb. 28, 1996.

(51) Int. Cl.[7] ............... C05F 11/08; C12N 1/00; C12N 1/20; C12N 1/14
(52) U.S. Cl. ............... 71/6; 47/DIG. 10; 71/11; 71/23; 71/24; 71/27; 71/28; 71/33; 71/34; 71/64.1; 435/243; 435/252.5; 435/254.6
(58) Field of Search ............... 71/6, 8, 24, 26, 71/23, 27, 28, 11, 33, 34, 64.1; 435/243, 252.5, 254.6; 47/DIG. 10

(56) References Cited

U.S. PATENT DOCUMENTS

| | | | | |
|---|---|---|---|---|
| 4,036,627 A | * | 7/1977 | Funk | 71/29 |
| 4,158,558 A | * | 6/1979 | Thompson et al. | 71/34 |
| 4,952,229 A | * | 8/1990 | Muir | 71/7 |
| 5,147,441 A | * | 9/1992 | Megeed | 71/7 |
| 5,201,930 A | * | 4/1993 | Campbell | 71/23 |
| 5,797,976 A | * | 8/1998 | Yamashita | 71/26 |

FOREIGN PATENT DOCUMENTS

| | | | | |
|---|---|---|---|---|
| FR | 2571717 | * | 6/1984 | 71/6 |

* cited by examiner

*Primary Examiner*—Wayne A. Langel
(74) *Attorney, Agent, or Firm*—St. Onge, Steward, Johnston and Reens LLC

(57) ABSTRACT

Shelf-stable soil enrichment solutions contain beneficial soil and plant microbial spores or colonies, e.g. Bacillus bacteria and/or Trichoderma fungal species, that remain at least about 90% viable for at least 12, preferably 18, months at room temperature. Preferred solutions are colloidal in nature and typically contain humic acid or other organic macromolecules, and exhibit a low salt index.

22 Claims, 1 Drawing Sheet

LIQUID SOIL ENRICHMENT MICROBIAL COMPOSITIONS

RELATED APPLICATION DATA

Figure 1:
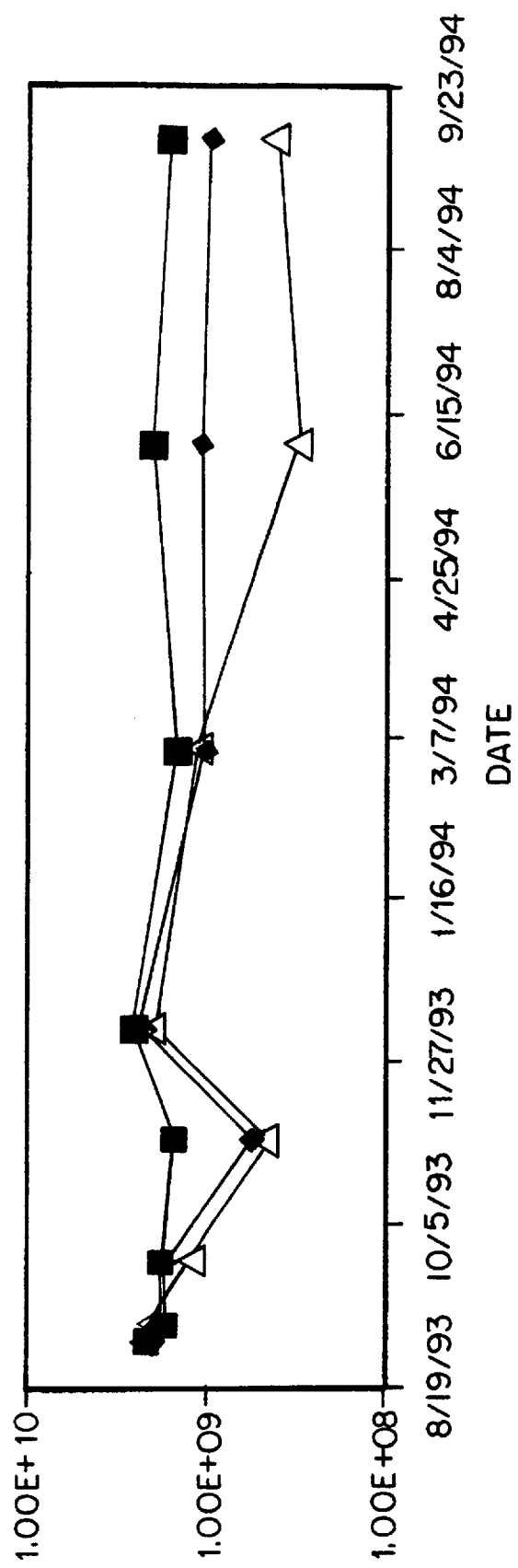

This application is a continuation-in-part of U.S. patent application Ser. No. 60/012,464, filed Feb. 28, 1996, which is incorporated in its entirety herein by reference.

TECHNICAL FIELD

This invention relates to shelf-stable soil enrichment solutions containing Bacillus and other spores.

BACKGROUND OF THE INVENTION

Where inoculations with microbes are required for agricultural uses such as soil enrichment, particularly enrichment of marginally suitable soils, control of insect pests, nematodes, and fungal disease, composting, and the like, dried preparations in the form of powders or granules are conventionally used because microorganisms lose viability in stored solutions. Typical liquid products containing microbes have an average short shelf life of only a few days to up to no more than about three weeks. Even so, liquid preparations are preferred for some applications because solutions are readily taken up by plants and can be formulated for controlled coverage by spray applicators. So solutions containing microorganisms are typically mixed just prior to use. See, for example, the addition of *Streptomyces griseaviridis* strains to aqueous suspensions in U.S. Pat. No. 4,595,589 to Tahvonen and Bacillus and Chlorella species to kelp extract products in U.S. Pat. No. 4,666,497 to Tenzer.

A number of attempts have been made to stabilize microorganisms in solution. Hettrick reported that reversible dormancy in a population of active microorganisms was achieved by adding diatomacious earth to the preparation (U.S. Pat. No. 3,898,132). Lewis disclosed ergot spore storage in at least about 25%, preferably between about 45 to 60%, by weight sugar solutions. In U.S. Pat. No. 4,161,397 to Bellet and Joshi, microdried bacteria were added to an oil carrier. In U.S. Pat. No. 5,366,532 to Fages, et al., microorganisms isolated from the rhizosphere such as *Azospirillum lipoferum* were microencapsulated in a polysaccharide matrix and packaged with a fertilizer.

Long-term storage stability in solutions at room temperature was apparently not achieved by these preparations, however. For example, the Fages, et al., results illustrate a viability decrease by a factor of five after 1 month of storage (column 3, line 43). Similarly, Barach and Kamara, who used polyethylene glycol or sodium alginate to stabilize acid-producing bacteria in buffer, typically observed a factor of 10 loss after 15 to 18 days (U.S. Pat. No. 4,720,460, column 5, line 68, column 6, line 44, and column 7, lines 11 to 12). In U.S. Pat. No. 3,999,973, Templeton disclosed a *C. malvarum* spore concentrate that maintained an 80% germination rate for up to 21 days if stored in ice.

It would be desirable to have soil enrichment solutions containing microorganism spores that remain viable for the shelf life of commercial stored agricultural products, i.e., at least about a year at room temperature.

SUMMARY OF THE INVENTION

It is an object of the invention to provide solutions that contain microorganism spores and/or colonies that remain viable for at least about a year when stored at room temperature.

It is another object of the invention to provide soil enrichment solutions containing viable microorganism spores and/or colonies, particularly those useful for enriching poor, disturbed soils or soils having little or no microbial activity because of the heavy past use of chemicals and/or fertilizers.

It is an additional object of the invention to provide solutions containing viable micro organism spores and/or colonies of beneficial fungicides that can be used for seed, turf, and leaf treatment for the prevention, control, and/or cure of turf and plant diseases and other beneficial purposes.

It is a further and more specific object of the invention to provide soil enrichment solutions containing microorganism spores and/or colonies that remain at least about 90% viable f or up to at least about 12, preferably 18 months at room temperature, i.e., about 20° to 25° C.

These and other objects are achieved by the present invention, which provides a method of preserving and solutions containing microbial spores and/or colonies comprising adding a microbial spore preparation such as lyophilized spores and/or colonies to a solution that is colloid al in nature and exhibits an ionic strength, water activity, and pH formulated to preserve the spores and/or colonies at room temperature. Typical soil enrichment solutions of the invention contain humic acids or another organic macromolecules such as methylene urea polymers having varying chain lengths that enhance spore/colony preservation. In some preferred embodiments, solutions of the invention are liquid fertilizers having a pH of less than or equal to about 3.5, and contain at least about 5% by weight humic acid or related macromolecules or other organic polymers, at least about 7% by weight cellulose fiber, at least about 1% carbohydrate, and at least about 1% by weight amino acids. The carbohydrates and amino acids are derived from plant extracts such as kelp extracts in some embodiments. Typical embodiments are formulated to deliver a range of from about 89 lb to about 176 lb nitrogen/acre/year for agricultural applications, and from about ⅛ lb to about 1 lb nitrogen per 1000 square feet for turf applications, with a total of about 4 to about 6 lb applied annually.

Spores and/or colonies that enrich soils and/or provide plant biological control agents are employed in preferred embodiments. These include bacteria such as Bacillus species, e.g., *Bacillus subtilis, Bacillus cereus, Bacillus penetrans, Bacillus licheniformis*, and *Bacillus megaterium*; fungi such as Trichoderma, e.g., *Trichoderma hamatum, Trichoderma harzianum, Trichoderma polysporum, Trichoderma konigii, Trichoderma viride*; yeast such as *Saccharomyces cerevisiae*; and mixtures of these. Other examples are given hereafter.

BRIEF DESCRIPTION OF THE FIGURE

FIG. 1 is a line graph showing the stability of two Bacillus strains in three solutions of the invention: a 30-0-0 slow release nitrogen liquid fertilizer containing methylene ureas of varying chain lengths (-◆-), a 18-3-6 slow release nitrogen liquid fertilizer containing micronutrients (-■-), and Essential™, a liquid natural organic fertilizer (-Δ-).

DETAILED DESCRIPTION OF THE INVENTION

The present invention relates to solutions that are formulated to preserve microbial spores and/or colonies at room temperature for extended periods. In particular, the invention relates to solution supplements for application to soil or foliage and methods of improving soil and plant productivity and quality. Soil enrichment solutions of the invention stimulate plant growth, rejuvenate the soil, and promote the growth of beneficial soil microorganisms. Some embodiments also provide natural pathogens for the prevention, control and/or cure of turf and plant diseases and other purposes encouraging germination and/or growth.

Any microbial spores and/or colonies can be preserved using methods and solutions of the invention. Spores and/or colonies of beneficial soil and plant pathogen biological control microorganisms are preferred. Microorganisms that grow rapidly and colonize substrata in soil after treatment with compositions of the invention are particularly preferred. These include, but are not limited to bacteria, e.g., Bacillus species such as *Bacillus subtilis, Bacillus cereus, Bacillus penetrans, Bacillus licheniformis*, and *Bacillus megaterium*; fungi, e.g., Trichoderma species such as *Trichoderma hamatum, Trichoderma harzianum, Trichoderma polysporum, Trichoderma konigii*, and *Trichoderma viride*; and yeast species such as *Saccharomyces cerevisiae*. As illustrated below, mixtures of microorganisms can also be preserved, and are preferred in many embodiments. Examples are given hereafter.

In the practice of the invention, spores or whole microorganisms, including harvested and/or lyophilized microbial colonies containing spores, are added to solutions. The solutions can be formulated for any use requiring viable microbial spores and/or colonies such as for fertilizers, composting, food products, and pharmaceutical compositions. Liquid fertilizers are preferred for soil enrichment purposes. Water miscible dry powders and/or granules such as lyophilized preparations of spores and/or colonies are preferred in many embodiments. The amount of spores or microorganisms added to solutions of the invention is not fixed per se, and necessarily is dependent upon the degree of soil and/or plant remediation required, the number and identity of microorganism species needed in the formulation, and the concentration of other ingredients in the formulation. Preferred embodiments employ spores and/or colonies in amounts effective to achieve recolonization of the soil by spray application of the composition. Typical embodiments contain sufficient spores and/or colonies to deliver from about 1000 to about 1,000,000 colony forming units (CFU) per square foot when the preparation is delivered.

Preservative solutions of the invention are colloidal in nature, containing humic acid and/or other organic macromolecules. By "colloidal" is meant a state of matter which comprises either large molecules, aggregations of smaller molecules, or a combination of the two. Typical embodiments contain large molecules such as humic acid and/or methylene urea compounds of varying chain length. The particles are surrounded by different matter such that a dispersed phase is surrounded by an external phase. Both phases may be solid or liquid (and sometimes gaseous). One phase comprises water in most embodiments; typical ranges are from about 35% to about 58% by weight water in the total composition, but some embodiments contain less than about 20% by weight water in the total composition.

Typical solutions contain at least about 5% by weight humic acid, at least about 7% by weight cellulose fiber, at least about 1% carbohydrate, and at least about 1% by weight amino acids. By "humic acid" is meant any of the complex allomelanin macromolecules having polymeric phenolic structures derived from humus, including soils, coals, and peat, that result from the decomposition of organic matter and that ordinarily chelate metals, particularly iron. Solutions containing humic acid, mixtures of humic acid with other acids derived from humus such as fulvic acid, potassium humate, and mixtures thereof are preferred in some embodiments. Humic acid concentrations of about 3.5 to 5.0 grams/liter are typical; at concentrations above about 12% by weight, e.g., 15%, the solutions have a tendency to gel.

The pH, ionic strength, and water activity of the solutions are selected to maximize the shelf life of spores and/or colonies stored in solution for at least a year, preferably at least 18 months, and minimize ionic exchange between the solutions and the spores and/or colonies. Preferred pHs are acidic, e.g., exhibit a pH of less than or equal to about 3.5, but higher pH solutions, e.g., from about 8 up to about 10, are employed in other embodiments. In some embodiments, the ionic strength of the solution is less than or equal to about 0.05 M.

Liquid fertilizer solutions that have been pasteurized are employed in some preferred embodiments. Some typical embodiments are formulated to deliver a range of from about 89 lb to about 176 lb nitrogen/acre/year for agricultural applications, and from about ⅛ lb to about 1 lb nitrogen per 1000 square feet for turf applications, with a total of about 4 to about 6 lb annually applied annually in these embodiments. As is known to skilled artisans, nitrogen requirements vary among different plant species, and application requirements vary with the method of application (soil, seed, and/or foliage), concentration of fertilizer, and seasonal variations, with other factors such as previous pest damage, drought and the like playing a role in what is optimal. Some warm season grass, for example, requires more nitrogen than cool season grass. In one embodiment described hereafter, a solution of the invention is formulated to slow deliver ½ pound of nitrogen per 1000 square feet. In this embodiment and others, the solution can contain methylene urea compounds of varying chain length or, as mentioned above, other organic polymers. Some embodiments contain surfactants that improve water absorption and retention and assist in the application and dispersion of the solution to foliage plants and seeds. These also assist adherence to foliage for extended periods, e.g. over a week and in some cases up to 5 weeks is preferred in some applications.

Solutions of the invention preferably contain intermediate metabolites, metabolites, simple sugars, peptides, amino acids, amides, enzymes, humates, lignin, organic chelates, and cellulose fiber derived from natural plant and animal products. Examples include, but are not limited to, commercial liquid fertilizers marketed under the trade names Nitro-30 SRN™ or Essentials, or mixtures of these. An advantage of these and related formulations useful in the practice of the invention is that they contain sugars, natural wetting agents, and the like useful to provide enhanced film adherence to plant tissue as mentioned above, so the products remain viable for extended periods. Examples are given hereafter.

While not wishing to be bound to any theory, it appears that a reason for the long term stability of microbial spores and/or colonies in solutions of the invention is related to the colloidal nature of the solution, which controls osmolality and osmotic pressure. Water becomes unavailable or physically entrained or occluded in solutions containing humic acid or other uncharged colloids and/or organic polymers, particularly large macromolecules. Moreover, as described above, many typical solutions of the invention contain less than about 20% water. Spores and/or colonies stored in these solutions remain viable in the absence of the osmotic stress that usually ruptures and destroys spores, causing a loss in viability.

A measure of this characteristic sometimes used in the fertilizer industry is called the "salt index" (herein denoted SI), which is a measure of the tendency of a fertilizer product to injure the seed or plant to which it is applied. The salt index is estimated by measuring the amount of electric current that a 1% solution will conduct. The higher the soluble salt content, the more current the product will conduct. The salt index of sodium nitrate is used as a standard product that will conduct; it has been assigned a standard reference point of 100, and other products are compared with it. Though there is some variation because various nutrient sources are more concentrated than others and burn potential is affected by the application rate and other factors as well as the salt index, typically, the higher the salt index, the higher the tendency of the product to cause injury to seed germination and plant growth. Most starter fertilizer products on the market that are recommended for placement on seeds, for example, have a salt index in the range of 40 to 50. Common fertilizers such as 9-18-9, 7-21-7, and 10-34-0 have salt indices of 40, 60, and 62, respectively, and many other commercial fertilizers, such as ammonium nitrate, sodium nitrate, and potassium chloride have higher salt indices as high as 105, 100, and 116 (respectively). Other illustrative examples include ammonium sulfate with a salt index of 69; potassium nitrate, 74; urea, 75; and potassium sulfate, 46. It is an advantage of the invention that preferred embodiments have a low salt index of less than about 35. Examples of fertilizers useful in the practice of the invention include, but are not limited to, natural organic fertilizers such as the ones described in the Examples that follow, which typically have a salt index of about 3.5 or less, monoammonium phosphate (SI~30), diammonium phosphate (SI~34), superphosphate (Ca$(H_2PO)_2$+$CaSO_4$, SI~7.8), triple superphosphate (Ca$(H_2PO_4)_2$, SI~10), monopotassium phosphate (SI~8.4), and the like, and mixtures thereof. One embodiment has a salt index of 0.

Microorganisms and/or their spores which can be preserved using formulations of the invention further exhibit a number of desirable characteristics related to soil enrichement and improvement of soil quality described above, such as biological control of plant pathogens (already mentioned); enhancement and/or production of desirable phtyohormones, e.g., auxins, giberillins and cytokinins; and solubilization of phosphates. Certain strains of *Bacillus subtilis*, for example, inhibit *N. Galligena* that colonize apple branch scars if applied to trees after leaf fall (Cook, R. J., and Baker, K. F., *The Nature and Practice of Biological Control of Plant Pathogens*, APS Press, St. Paul, Minn., 1983, pp. 308). *E. herbicola* and Pseudomonas isolates have been shown to partially control fire blight of pome fruit trees (ibid.). Several Bacillus species produce antibiotics useful when sprayed as a leaf or needle application on tobacco, Douglas fir, and apple trees, and the natural protection of leaves provided by the buffering capacity of phylloplane microorganisms has been demonstrated (id., at 216). Azobacter, Rhizobium, Bacillus, Klebsiella, Azospirillium, Enterobacter, Serratia, Agrobacterium, Arthrobacter, Aerobacter, Actinomyces, Bacillus, Pseudomonas, and other bacteria stimulate growth, increase yield, and produce other positive results by various mechanisms including enhancing nutrient uptake, increasing germination, enhancing seedling emergence, stimulating de novo biosynthesis, and the like, when applied to fields of various food plants (Frankenberger, W. T., and Arshad, *Phytohonnones in Soils, Microbial Production and Function*, Marcel Dekker, New York, 1995, pages 3 to 5, 20 to 21, and 36 to 37).

It is another advantage of the invention that preferred solutions supply carbon-rich organic materials in a bioavailable form for soils and plants together with nutrients that feed the microorganisms as they multiply after application. Solutions of the invention provide an excellent food source for the germination of spores and/or colonies when the solutions are applied to soil or foliage. It is a further advantage of the invention that preferred solutions contain a wide variety of naturally occurring metabolites that can be readily absorbed by the growing microorganisms and enhance seed germination, root development, and growth of plants in the soil.

As summarized above, it is a further advantage of the invention that some embodiments are formulated with microorganism spores and/or cultures useful in the prevention, control and/or cure of plant diseases, particularly those of fungal origin. Illustrative examples are provided hereafter. One embodiment, for example, maintains the viability of *Bacillus subtills* GB03 (EPA Reg. No. 7501-144), a bacteria recognized to colonize developing root systems, suppressing disease organisms such as Fusarium, Rhizoctonia, Alternaria and Aspergillus that attack root systems. Compositions of the invention can be used to treat developed root systems as well as developing root systems. As the root system develops, grows, and functions, the bacteria grow with the roots, extending protection throughout the growing season. As a result of this biological protection, a vigorous root system can be established and maintained by the plants.

In addition, *B. subtilis* GB03 has been shown to increase the amount of nodulation by nitrogen-fixing bacteria when used on many legumes. This improvement in nodulation is a result of a healthier root system, allowing more sites for nodules to form from naturally-occurring soilborne nitrogen-fixing bacteria. Illustrative examples follow.

EXAMPLES

The following examples are presented to further illustrate and explain the present invention and should not be taken as limiting in any regard. Unless otherwise indicated, all percentages are by weight, and relate to the weight percentage of the particular processing step described.

Example 1

Microorganisms were stabilized in three solutions in this example. Solution 1 is Nitro-30 SRN™, a 30-0-0 80 to 85% slow release nitrogen fertilizer product containing methylene ureas of varying chain lengths. It has a pH of 8.5 has a very low salt index, and very low phytotoxcity to plant materials. A dry microorganism preparation containing *Bacillus subtilis, Bacillus licheniformis*, and *Bacillus megaterium* (454 billion to 2 trillion culture forming units (CFU)/lb), *Saccharomyces cerevisiae* (250 billion cells/lb), cellulase (21,000 filter paper units (FPU)/lb), pectinase (6500 apple pomace (APU)/lb), protease not less than 2500 CSU/lb in a water miscible powder available as an inoculant under the trademark ENVIROMATE a product of CHR, Hansen's Laboratory Inc. of Milwaukee, Wis., was added to solution 1 in a ration of about 2.5 lbs/ton liquid fertilizer, i.e., sufficient to yield a microbial application rate of more than 1 million CFU of Bacillus per square foot if the application rate of the fertilizer is ½ lb nitrogen per 1000 square feet. The microoganisms remained 98% viable for 18 months. Similar results were obtained with a 28-0-0 liquid fertilizer.

The same microorganisms were added to a liquid 18-3-6 50% slow release nitrogen fertilizer (solution 2) at a rate of 1.75 lbs/ton fertilizer. Based on an application rate of ½ lb of nitrogen per 1,000 square feet, this corresponds to the additional application of about 1 million CFU of Bacillus. The samples were monitored and checked for viability at regular intervals. Samples remained 98% viable for 18 months.

The same microorganism preparation was added to solution 3, Essential™, a natural organic fertilizer containing about 6% humic acid, 10% cellulose fiber, 1.2% lignin, 3% mono/disaccharides, 0.1% kelp extract, 2% carbohydrates, 0.0025% natural wetting agents, 13.17 mg/lb riboflavin, 0.314% vitamin B6, and 4.21% minerals and other chemicals (Fe, Ca, Mn, Mg, Zn, Cu, I, B, S, P, K, and N) at a rate of about 4.75 lbs/ton. The ash content of the fertilizer is about 2% and amino acid constitutents from plant extracts, kelp extract, and other proteins typically comprise about 0.39% glutamic acid, 0.1% threonine, 0.35% aspartic acid, 0.16% serine, 0.19% protein, 0.02% methionine, 0.53% glycine, 0.26% alanine, 0.1% valine, 0.08% phenylalanine, 0.07% isoleucine, 0.01% tyrosine, 0.17% leucine, 0.12% arginine, 0.16% lysine, 0.04% histidine, 0.12% arginine, and trace amounts of β-alanine, cystine, and taurine. If about 4 oz of the fertilizer is applied per 1,000 square feet, about 1 million CFU of Bacillus is applied per square foot. Samples remained viable at 98% for 18 months.

Cultures of two strains of *Bacillu subtils*, CH200 and CH201, were tested in the same three solutions, and the following plating results were obtained (expressed as CFU/g Bacillus spores):

Example 3

This example provides information about the utility of compositions of the invention as a treatment for plant fungi disease.

One study evaluated brown patch fungicides on irrigated perennial ryegrass at the Michigan State University campus during the summer months. The grass was maintained at a height of 1.5 inches and was fertilized with 2 lb nitrogen per 1000 square foot per month to promote disease. Plots were 2'4.5', with 1' alleys between rows. Four replications of each treatment were made. Brown patch plots were inoculated with *Rhizoctonia solani* growing on a cornmeal/sand mixture to encourage uniform disease development. Plots were covered with plastic greenhouse trays in the evenings to maintain high humidity during the night. The trays were removed in the mornings.

In the study, 4 fl oz compositions of the invention marketed under the name Companion™ and Companion 2™ were applied per 1000 $ft^2$ at 14day intervals. As standards, Daconil Ultrex™ and Thalonil™ (4L) were applied, also at 14-day intervals, to grass patches at levels of 3.8 oz/1000 $ft^2$ and 6 oz/1000 $ft^2$, respectively. Patches were rated on a scale which evaluated the percent area under each infected pan after 40 days. The average LSD for the four squares treated with Companion™ was 22.5% and Companion 2™ was 32.5%, while the corresponding averages for Daconil Ultrex™ and Thalonil™ were 0.5% and 3.0%, respectively.

LAB REQ. WFS 090193    GROWTH PRODUCTS, INC.
STABILITY OF CH200 & CH201 IN LIQUID FERTILIZER AT ROOM TEMPERATURE

| | Date plated 9/3/93 | 9/8/93 | 9/27/93 | 11/3/93 | 12/7/93 | 3/3/94 | 6/6/94 | 9/7/94 |
|---|---|---|---|---|---|---|---|---|
| Soluton 1 | 1.81E + 09 | 1.73E + 09 | 1.68E + 09 | 5.67E + 08 | 2.33E + 09 | 1.04E + 09 | 1.09E + 09 | 9.73E + 08 |
| Soluton 2 | 2.28E + 09 | 1.78E + 09 | 1.85E + 09 | 1.57E + 09 | 2.60E + 09 | 1.48E + 09 | 2.01E + 09 | 1.64E + 09 |
| Soluton 3 | 2.24E + 09 | 2.21E + 09 | 1.24E + 09 | 4.70E + 08 | 1.98E + 09 | 1.16E + 09 | 3.07E + 08 | 4.27E + 08 |

All counts are given in CFU/g - Bacilius spore

NOTE: At 16 months an attempt was made to do another plating. The Nitro 28 sample had become one solid mass, the 18-3-6 Liquid Fertilizer sample had produced an 1" sediment layer (dead cells), and the Essential sample appeared the same as a T-O. These findings were reported and a decision was made to terminate this stability.

Results are plotted in FIG. 1. It can be seen from the data that spores remain viable for extended periods in solutions of the invention.

Example 2

The physical characteristics of some solutions useful in the practice of formulating compositions of the invention are given in this example.

Salt indices for compositions of the invention were determined using Standard Method Leco FP428, *Soil Ch. Anly.*, Jackson, p. 245, which has a detection limit of 0.01. Two solutions of the invention containing 30.4% (Nitro-30™ of Example 1) and 26.9% total nitrogen, respectively, and exhibited no detectable salt index, and a third having 10.4% total nitrogen exhibited a salt index of 32. A 18-3-6 fertilizer had a salt index of 17, another sample of Nitro-30™ (total nitrogen=28.94%) had a salt index of 2, and Triple Ten (total nitrogen=10.75%) had a salt index of 26.

The average Brookfield viscosity of Nitro-30™ at 25° C. was 15 to 30 centipoise. The specific gravity of the same product averaged 1.249 (range=1.24 to 1.26) when measured with a hydrometer at 25° C. The pH at the same temperature was 10.1.

Compared to untreated controls exhibiting full infection, the results showed a significant reduction in brown patch using compositions of the invention.

Similar experiments were repeated at Rutgers University in a summer field evaluation of another turf grass disease, dollar spot. Fungicides were applied to four plots, and the results were averaged. Companion 2™ was applied as a spray at a level of 4.0 fl oz/1000 $ft^2$ on a 28-day schedule for two treatments, and then on a 14-day schedule for two treatments. The number of lesion centers per plot in four replicates fell from 43.0 to 31.0 to 26.5 at intervals over the course of the eight-week study. Over the same period and at the same intervals, untreated control plots exhibited 68.5, 69.2, and 39.5 lesion centers/plot. Over the same period, Daconil Ultrex™, applied 0.95 oz/1000 $ft^2$ at 14-day intervals, exhibited 43.2, 28.2, and 33.2 lesions/plot when counted at the same intervals. The results clearly show the fungicide properties of compositions of the invention.

In addition, a strain of *B. subtilis*, GB03 (EPA Reg. No. 7501-144), known to be useful as a fungicide was tested for viability in a composition of the invention in a manner set out in Example 1 above. The strain remained viable for about 18 months.

Example 4

This example illustrates the film adherence of some embodiments of the invention.

Nitro-30™ employed in Example 1 was used as a foliar spray The undiluted product had a density of 1.23 g/cm³, a pH of 8.2 to 8.5, a viscosity of 0.8 to 3.5 pa x s, and a salt index of 30. When applied at an application rate of 0.5% to 4% to hops, apples, azeleas, rhododendron, pelargonium, tobacco, and tomato plants, shrubs or trees, the solution provided a slow release fertilizer that remained on the leaf tissue for up to 5 weeks.

The above description is for the purpose of illustrating and not limiting the present invention, and teaching the person of ordinary skill in the art how to practice the invention. It is not intended to detail all those obvious modifications and variations of it which will become apparent to the skilled worker upon reading the description. It is intended, however, that all such obvious modifications and variations be included within the scope of the present invention as defined in the appended claims. The claims are meant to cover the claimed components and steps in any sequence which is effective to meet the objectives there intended, unless the context specifically indicates the contrary.

The patents, papers, and book excerpts cited above are hereby incorporated herein by reference in in their entireties.

What is claimed is:

1. A method of preserving a liquid microbial preparation comprising adding a microbial preparation to a solution having a colloidal nature and containing humic acid, cellulose fiber, carbohydrates, and amino acids, to form a composition exhibiting a salt index of less than about 35, such that the composition retains a microbial viability of at least about 19% for a period of about a year at room temperature.

2. A method according to claim 1 wherein the composition exhibits a salt index of about 35 or less.

3. A method according to claim 1 wherein the microbial preparation is selected from the group consisting of a lyophilized, water-miscible spore preparation, colony preparation, and mixtures thereof.

4. A method according to claim 1 wherein the microbial preparation comprises species selected from the group consisting of Bacillus, Trichoderma, Saccharomyces species, and mixtures thereof.

5. A method according to claim 1 wherein the solution has a pH of less than or equal to about 3.5, or a pH of about 8 to about 10.

6. A method according to claim 1 wherein the solution is a fertilizer solution formulated to deliver at least about ½ a pound of nitrogen per 1000 square feet.

7. A composition prepared according to the method of claim 1.

8. A liquid composition comprising a microbial spore or culture preparation and a solution having a colloidal nature and containing humic acid, cellulose fiber, carbohydrate, and amino acids, and having an osmolality, viscosity, water content and salt index such that the microbial preparation remains at least about 19% viable for at least about 12 months when stored at room temperature.

9. A composition according to claim 8 which exhibits a salt index of about 35 or less.

10. A composition according to claim 9 further comprising a fertilizer having a salt index of about 35 or less.

11. A composition according to claim 8 wherein the microbial spore and culture preparation is selected from the group consisting of spores or cultures selected from the group consisting of Bacillus, Trichoderma, Saccharomyces species, and mixtures thereof.

12. A composition according to claim 11 wherein the Bacillus species is selected from the group consisting of *Bacillus subtilis, Bacillus cereus, Bacillus penetrans, Bacillus licheniformis, Bacillus megaterium*, and mixtures thereof.

13. A composition according to claim 11 wherein the Trichoderma species is selected from the group consisting of *Trichoderma hamatum, Trichoderma harzianum, Trichoderma polysporum, Trichoderma konigii, Trichoderma viride* and mixtures thereof.

14. A composition according to claim 11 wherein the microbial preparation is a lyophilized, water-miscible spore preparation.

15. A composition according to claim 8 wherein the solution contains methylene urea compounds of varying chain length.

16. A composition according to claim 8 wherein the solution contains humate.

17. A composition according to claim 8 which exhibits soil enrichment properties when applied to soil.

18. A composition according to claim 8 which biologically controls plant pathogens when applied to soil or plants.

19. A soil enrichment composition comprising a lyophilized, water-miscible microbial spore or culture preparation and a solution having a colloidal nature, and containing at least about 5% by weight humic acid, at least about 7% by weight cellulose fiber, at least about 1% carbohydrate, and at least about 1% by weight amino acids;

wherein said carbohydrates and amino acids are derived from plant extracts;

wherein said spore or culture preparation remains at least about 19% viable for at least 12 months when stored at room temperature; and also wherein the composition exhibits a salt index of about 35 or less.

20. A composition according to claim 19 which further exhibits biological control of plant pathogens.

21. A composition according to claim 19 containing less than or equal to about 35% water.

22. A soil enrichment composition comprising:

a lyophilized, water-miscible microbial spore or culture preparation and a solution having a colloidal nature, and containing at least about 5% by weight humic acid, at least about 7% by weight cellulose fiber, at least about 1% carbohydrate, and at least about 1% by weight amino acids;

wherein said carbohydrates or amino acids are derived from plant extracts;

wherein said spore and culture preparation remains at least about 90% viable for at least 12 months when stored at room temperature; and also wherein the composition exhibits a salt index of about 35 or less.

* * * * *